United States Patent
Buchalova et al.

(10) Patent No.: US 11,337,908 B2
(45) Date of Patent: May 24, 2022

(54) PERSONAL CARE COMPOSITIONS WITH CYSTINE

(71) Applicant: Conopco, Inc., Englewood Cliffs, NJ (US)

(72) Inventors: Maria Buchalova, Sandy Hook, CT (US); Teanoosh Moaddel, Watertown, CT (US); Qiang Qiu, Easton, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/470,513

(22) PCT Filed: Dec. 18, 2017

(86) PCT No.: PCT/EP2017/083223
§ 371 (c)(1),
(2) Date: Jun. 17, 2019

(87) PCT Pub. No.: WO2018/114749
PCT Pub. Date: Jun. 28, 2018

(65) Prior Publication Data
US 2020/0222293 A1    Jul. 16, 2020

Related U.S. Application Data

(60) Provisional application No. 62/437,261, filed on Dec. 21, 2016.

(51) Int. Cl.
*A61K 8/44* (2006.01)
*A61K 8/02* (2006.01)
*A61K 8/04* (2006.01)
*A61K 8/36* (2006.01)
*A61Q 19/00* (2006.01)

(52) U.S. Cl.
CPC ............ *A61K 8/447* (2013.01); *A61K 8/0295* (2013.01); *A61K 8/042* (2013.01); *A61K 8/361* (2013.01); *A61Q 19/00* (2013.01); *A61K 2800/10* (2013.01); *A61K 2800/412* (2013.01); *A61K 2800/805* (2013.01)

(58) Field of Classification Search
None
See application file for complete search history.

(56) References Cited

U.S. PATENT DOCUMENTS

| | | |
|---|---|---|
| 3,274,063 A | 9/1966 | Nieper |
| 3,786,076 A | 1/1974 | Morelle |
| 3,819,825 A | 6/1974 | Goodwin |
| 4,201,235 A | 6/1980 | Ciavatta |
| 4,707,354 A | 11/1987 | Garlen et al. |
| 4,801,579 A | 1/1989 | Rainer et al. |
| 4,885,157 A | 5/1989 | Fiaschetti |
| 5,133,958 A | 7/1992 | Stuckler |
| 5,137,714 A | 8/1992 | Scott |
| 5,198,465 A | 3/1993 | Dioguardi |
| 5,254,331 A | 10/1993 | Mausner |
| 5,416,075 A | 5/1995 | Carson |
| 5,472,706 A | 5/1995 | Friedman |
| 5,582,817 A | 10/1996 | Otsu |
| 5,667,768 A | 9/1997 | Ramin |
| 5,679,819 A | 10/1997 | Jones |
| 5,887,747 A | 3/1999 | Burklin et al. |
| 6,013,279 A | 11/2000 | Klett-Loch |
| 6,149,925 A | 11/2000 | Mammone |
| RE37,934 E | 12/2002 | Hoffmann |
| 6,602,492 B2 | 5/2003 | Iwasaki |
| 6,592,908 B1 | 7/2003 | Crum |
| 6,858,217 B2 | 2/2005 | Kerschner |
| 6,869,598 B2 | 3/2005 | Love et al. |
| 6,863,897 B2 | 8/2005 | Love et al. |
| 6,992,062 B2 | 1/2006 | Usala |
| 7,105,570 B2 | 12/2006 | Iwasaki |
| RE39,734 E | 7/2007 | Crum |
| 7,300,649 B2 | 11/2007 | Tanojo |
| 7,427,640 B1 * | 9/2008 | Katayama ............ A61K 8/375 424/401 |
| 7,740,831 B2 | 6/2010 | Chiba |
| RE42,645 E | 8/2011 | Crum |
| 8,119,111 B2 | 2/2012 | Malek |
| 8,241,681 B2 | 8/2012 | Herrmann |
| 8,299,127 B2 | 10/2012 | Anjing et al. |
| 8,357,649 B2 | 1/2013 | Chieffi |
| 8,361,446 B2 | 1/2013 | Muller |
| 8,440,172 B2 | 5/2013 | Johncock |
| 8,722,026 B2 | 5/2014 | Niki |
| 8,735,442 B2 | 5/2014 | Ashida et al. |
| 8,795,643 B1 | 5/2014 | Anthony |
| 8,815,800 B2 | 8/2014 | Pashkovski |

(Continued)

FOREIGN PATENT DOCUMENTS

| | | |
|---|---|---|
| CA | 2337772 | 1/2000 |
| CN | 1758935 | 4/2006 |

(Continued)

OTHER PUBLICATIONS

English translation of CN 101 797 213 (Year: 2010).*
Tareen; The Effects of a Glutathione Precursor FT061452 on Serum and Intracellular Glutathione Levels; ClinicalTrials.gov The Effects of a Glutathione Precursor FT061452 on Serum 2013; 2013; .; .; United States of America.
Mela BB Cream Pact IRF 35 SPF 50+/PA+++, Mintel Database GNPD; 2014; XP002778757; pp. 1-5; Korea (South).
Hydrating Mask; Mintel Database GNPD; Aug. 1, 2014; XP002778756; pp. 1-3.

(Continued)

*Primary Examiner* — Sin J Lee
(74) *Attorney, Agent, or Firm* — Stephanie S. DelPonte

(57) ABSTRACT

Personal care topical compositions at skin-tolerant pH with cystine which is solubilized or has small crystal size below 20 microns. A process of making the composition is also described.

9 Claims, No Drawings

(56) References Cited

U.S. PATENT DOCUMENTS

| | | |
|---|---|---|
| 8,865,143 B2 | 10/2014 | Lu |
| 9,849,079 B2 | 12/2017 | Smola et al. |
| 2003/0194417 A1 | 10/2003 | Iwasaki |
| 2005/0192229 A1 | 1/2005 | Perricone |
| 2005/0271726 A1 | 12/2005 | Crum |
| 2006/0063718 A1 | 3/2006 | Perricone |
| 2006/0257351 A1 | 11/2006 | Chiba |
| 2007/0213243 A1* | 9/2007 | Yao ................. C11D 3/042 510/130 |
| 2008/0274068 A1 | 11/2008 | Tamaka et al. |
| 2009/0263513 A1 | 10/2009 | Marini |
| 2010/0305169 A1 | 12/2010 | Robinson |
| 2010/0322876 A1 | 12/2010 | Nguyen |
| 2011/0183040 A1 | 7/2011 | Ermolin |
| 2011/0195103 A1 | 8/2011 | Perz Arcas |
| 2012/0034183 A1 | 2/2012 | Cohen |
| 2012/0214871 A1 | 8/2012 | Pehratovic et al. |
| 2013/0048567 A1* | 2/2013 | Tongesayi ............. C02F 1/28 210/670 |
| 2014/0065196 A1 | 3/2014 | Gabbay |
| 2014/0162979 A1* | 6/2014 | Palla-Venkata ........ A61K 8/463 514/63 |
| 2015/0064122 A1 | 3/2015 | Meyer et al. |
| 2015/0342854 A1 | 12/2015 | Shibuya |
| 2016/0120782 A1 | 5/2016 | Lee |
| 2016/0250241 A1 | 9/2016 | Deren-Lewis |
| 2017/0079895 A1 | 3/2017 | Edelson et al. |
| 2017/0112764 A1 | 4/2017 | Wu |
| 2020/0016059 A1* | 1/2020 | Guelakis ................. A61K 8/46 |
| 2020/0108002 A1 | 4/2020 | Damodaran et al. |

FOREIGN PATENT DOCUMENTS

| | | |
|---|---|---|
| CN | 101773458 | 7/2010 |
| CN | 101797213 | 11/2010 |
| CN | 102150866 | 8/2011 |
| CN | 102366397 | 3/2012 |
| CN | 103442678 | 12/2013 |
| CN | 103957867 | 7/2014 |
| CN | 104302271 | 1/2015 |
| CN | 105147590 | 12/2015 |
| CN | 105919827 | 7/2016 |
| CN | 107411982 | 12/2017 |
| EP | 0815040 | 10/1996 |
| EP | 1269978 | 1/2003 |
| EP | 2572701 | 3/2013 |
| EP | 2921160 | 9/2015 |
| EP | 3103434 | 12/2016 |
| FR | 2608424 | 6/1988 |
| FR | 2660196 | 10/1991 |
| FR | 2997852 | 5/2014 |
| GB | 720561 | 12/1954 |
| GB | 874368 | 8/1961 |
| GB | 987800 | 3/1965 |
| GB | 1050756 | 12/1966 |
| GB | 2212722 | 8/1989 |
| JP | 61227515 | 10/1986 |
| JP | 5032533 | 2/1993 |
| JP | 6128143 | 5/1994 |
| JP | 2009242321 | 10/2009 |
| JP | 2010280675 | 12/2010 |
| JP | 2011524393 | 9/2011 |
| JP | 2014505712 | 3/2014 |
| JP | 2014080384 | 5/2014 |
| JP | 2014196275 | 10/2014 |
| JP | 2015030689 | 2/2015 |
| JP | 2015205859 | 11/2015 |
| JP | 2006001903 | 1/2016 |
| JP | 2016033116 | 3/2016 |
| KR | 20160123753 | 10/2016 |
| WO | WO9505852 | 3/1995 |
| WO | WO9913819 | 3/1999 |
| WO | WO0003689 | 1/2000 |
| WO | WO0025740 | 5/2000 |
| WO | WO0069403 | 11/2000 |
| WO | WO03080011 | 10/2003 |
| WO | WO03105806 | 12/2003 |
| WO | WO04082654 | 9/2004 |
| WO | WO2004103353 | 12/2004 |
| WO | WO2005097060 | 10/2005 |
| WO | WO2007021065 | 2/2007 |
| WO | WO2007070069 | 6/2007 |
| WO | WO2010090546 | 8/2010 |
| WO | WO2010113925 | 10/2010 |
| WO | WO2011155280 | 12/2011 |
| WO | WO2012002669 | 1/2012 |
| WO | WO2012094638 | 7/2012 |
| WO | WO2013044111 | 3/2013 |
| WO | WO1309250 | 6/2013 |
| WO | WO2015005563 | 1/2015 |
| WO | WO2016033183 | 3/2016 |
| WO | 105919827 | 9/2016 |
| WO | WO2016178944 | 11/2016 |

OTHER PUBLICATIONS

Kumano et al.; Studies of water-in-oil (w/o) emulsion stabilized with amino acids or their salts; Journal Society Cosmetic Chemists; 1977; pp. 285-314; XP001058465; vol. 28, No. 5.

Tareen; The Effects of Short Term Adminstration of a Novel Glutathione Precursor (FTO61452) . . . ; RTRN Research Hub 2012 pp. 1-2; 2012; 1-2; .

Search Report and Written Opinion in PCTEP2017083207; dated Mar. 19, 2018.

L-Cystine; Sigma-Aldrich Product Information C8755.

Meister; Selective Modification of Glutathione Metabolism; Science 200 vol. 220 1985 pp. 471-477; 1985; pp. 471-477; 220.

Meister, Alton; Glutathione Metabolism and Its Selective Modification; J Biol Chem; Nov. 25, 1988; pp. 17205-17208; vol. 263, No. 33.

IPRP2 in PCTCN2017117008; Apr. 22, 2019; .

Search Report and Written Opinion in PCTCN2017117008; dated Mar. 27, 2018; .

Constantinides et al.; Enhanced intestinal absorption of an RGD peptide from water-in-oil microemulsions of different composition and particle size; Journal of Controlled Release; 1995; 109-116; vol. 34.

Search Report and Written Opinion in EP18173916; dated Oct. 23, 2018; .; European Patent Office (EPO).

Search Report in EP17156112; dated Apr. 7, 2017.

Dolphin; Glutathione: Chemical, biochemical and medical aspects; Cell Biochemistry & Function Apr. 1990 vol. 8 Issue 2 pp. 139; Apr. 1990; 139; vol. 8, Iss 2; United States of America.

Meister; Glutathione Metabolism and Its Selective Modification; The Journal of Biological Chemistry ; 1988; pp. 17205-17208; vol. 263 No. 33; United States of America.

Tyrrell; Correlation Between Endogenous Glutathione Content and Sensitivity of CulturedHuman Skin Cells . . . ; Photochemistry and Photobiology 1988 vol. 47 No. 3 pp. 405-412; 1988; p. 405-412; vol. 47, No. 3; United States of America.

Search Report and Written Opinion in EP16169468; dated Oct. 14, 2016; .

Search Report & Written Opinion in EP17156128; dated Apr. 7, 2017.

Search Report and Written Opinion in PCTEP2017083223; dated Mar. 23, 2018.

Molding Cream; Mintel GNPD; 2005; pp. 1-2; XP002778899.

Ja Yoon Cream; Mintel GNPD; 2016; pp. 1-6; XP002778901.

Frizz and Stray Hair Control Cream; Mintel GNPD; 2006; pp. 1-2; XP002778900.

Written Opinion in PCTEP2017083207; .

Written Opinion 2 in PCTEP2017083223; dated Jan. 15, 2019.

Anonymous; Conditioner; Mintel GNPD Conditioner; Mar. 22, 2007; pp. 1-2; XP055522806.

Anonymous; Shape & Life Volumising Gel; Mintel GNPD Shape & Lift Volumising Gel; Apr. 11, 2007; pp. 1-2; XP055522803.

IPRP in PCTEP2017083207; Mar. 1, 2019.

Search Report and Written Opinion in PCTCN2017117015; dated Mar. 23, 2018; .

(56) References Cited

OTHER PUBLICATIONS

IPRP in PCTEP2017083223; Apr. 3, 2019.
Search Report and Written Opinion in PCTCN2017117006; dated Mar. 14, 2018; .
Search Report and Written Opinion in PCTCN2017116999; dated Mar. 20, 2018; .
IPRP2 in PCTCN2017117006; Apr. 25, 2019; .
IPRP2 in PCTCN2017116999; Apr. 26, 2019; .
IPRP2 in PCTCN2017117015; Apr. 26, 2019; .
Supplementary Search Report and Written Opinion in EP17883107; dated Dec. 11, 2019.
Search Report and Written Opinion in EP17882397; dated Aug. 27, 2019.
Supplemental Search Report and Written Opinion in EP17885031; dated Nov. 11, 2019.
Mintel GNPD; Hydra-Filler Pro-Youth Boosting Moisturizer; 2013; pp. 1-3 (Record ID 2117408).
Mintel GNPD; Hyal-Defence Hyaluronic Acid Protection Serum; 2012; pp. 1-3 (Record ID 1850085).
Co-Pending Application, Guelakis, et al, Jun. 17, 2019, U.S. Appl. No. 16/470,425.
Co-Pending Application, Damodaran, et al, Jun. 17, 2019, U.S. Appl. No. 16/470,391.
Co-Pending Application, Damodaran, et al, Jun. 17, 2019, U.S. Appl. No. 16/470,426.
Co-Pending Application, Guelakis, et al, Jun. 17, 2019, U.S. Appl. No. 16/470,439.
Co-Pending Application, Lou, et al, Jun. 17, 2019, U.S. Appl. No. 16/470,434.
Chol et al.; Glutathione precursors replenish decreased glutathione pool in cystinotic cell lines; Biochemical and Biophysical Research Communications; 2004; pp. 231-235; 324.
Search Report and Written Opinion in EP17882292, dated Jul. 23, 2020.
GNPD, Mintel Record, Meso-Maks Anti-Wrinkl Lightening Mask, Record ID2464407, XP55714586, pp. 1-4 (2014).
Quadro, Submicron Homogenizing, Quadro Engineering Corp., 2016; pp. 1-2.

\* cited by examiner

PERSONAL CARE COMPOSITIONS WITH CYSTINE

FIELD OF THE INVENTION

The invention relates to topical personal care compositions comprising cystine, and to methods of preparing them, wherein compositions are within the pH range suitable for application to skin and contain cystine.

BACKGROUND OF THE INVENTION

Topical personal care compositions must be formulated at a skin-tolerant pH range, but many of the cosmetically beneficial compounds have very low solubility at that pH, their solubility being substantially higher at a very alkaline or very acidic pH, outside of the pH range tolerated by skin. Some examples of such compounds are salicylic acid, fumaric acid, azelaic acid, sorbic acid, uric acid, alginic acid, amino acids and other zwitterionic compounds such as for example tyrosine, isoleucine, tryptophan, phenylalanine. One of such compounds, for example, is cystine. This is unfortunate because cystine can serve as a building block for glutathione production in the body. Glutathione (GSH) is a tripeptide that consists of glutamate, cysteine, and glycine. It is present in all mammalian tissues. It is the main anti-oxidant in the living body: it protects cells from oxidation by quenching reactive oxygen species. GSH is believed to play a significant role in protecting cells against the cytotoxic effects of ionizing radiation, heat, certain chemicals, and significantly, solar UV radiation (Tyrell et al., Photochem. Photobiol. 47: 405-412, 1988; Meister, J. Biol. Chem. 263: 205-217, 1988; Meister, Science 200:471-477, 1985). While true in all areas of the body, this is particularly important in the skin, which is so greatly exposed to the damaging effects of radiation, particularly UV radiation, and environmental pollutants. Decrease in the intracellular concentration of glutathione in skin is associated with cell damage, inflammation, skin darkening, discoloration, spots or freckles caused by exposure to ultraviolet radiation, physiological aging, and the like. It is, therefore, highly desirable to enhance the generation of glutathione in skin.

A logical approach would seem to be to provide cells with an exogenous source of GSH (e.g. through ingestion or topical delivery). Unfortunately, GSH is not bioavailable when administered exogenously, i.e. where localized extracellularly, it is broken down into its constituent amino acids (glutamate, cysteine, and glycine) for cellular uptake and synthesis of the GSH tripeptide. Thus, GSH is not directly transported into the cells and therefore does not itself result in an intracellular increase of glutathione. Biosynthesis of GSH occurs in the cell in a tightly regulated manner. The quantity of glutathione in cells depends to a large degree on the availability of cysteine in the cells. Cysteine, a composite amino acid of GSH, may increase cellular levels of GSH, but exposed sulfhydryl group of cysteine renders it unstable and reactive and also causes strong unpleasant odor. Unlike cysteine, cystine can be administered safely; cystine is transported into the cell and converted to cysteine within the cell, the cysteine then being available for intracellular GSH production.

Topical compositions containing various amino acids and other skin care actives have been described, see e.g. Tanojo U.S. Pat. No. 7,300,649, Laboratoire Filorga product, Schlachter WO 00/03689, Ermolin et al. US2011183040, Garlen et al. U.S. Pat. No. 4,707,354, Muller et al. U.S. Pat. No. 8,361,446, Hermann et al. U.S. Pat. No. 8,241,681. Compositions for potentiating intracellular glutathione production have been described. See e.g. Chiba et al. U.S. Pat. No. 7,740,831, Crum et al (USRE37934, USRE42645, WO2016/033183, and US20050271726); Mammone U.S. Pat. No. 6,149,925, and Perricone US 20060063718.

Cystine is normally derived from the diet. Delivery of cystine from topical compositions, however, is challenging due to its extremely low solubility in biologically acceptable vehicle at a skin-tolerant pH range. The solubility of cystine in water is 0.112 mg/ml at 25° C.; cystine is more soluble in aqueous solutions with pH less than 2 or pH above 8. Efforts have been made to increase L-Cystine solubility. See e.g. Erich Konigsberger, Zhonghua Wang, Lan-Chi Königsberger Solubility of L-Cystine in NaCl and Artificial Urine Solution; *Monatshefte für Chemie*, January 2000, Volume 131, Issue 1, pp 39-45; Hsieng-Cheng TsengHsieng-Cheng Tseng et.al, Solubilities of amino acids in water at various pH values under 298.15 K, Fluid Phase Equilibria 285(1): 90-95 October 2009; F. Apruzzese, et.al Protonation equilibria and solubility of L-Cystine, Talanta, 56, 459-469, 2002; C. Bretti, et.al Solubility and activity coefficients of acidic and basic noneelectrolytes in aqueous salt solutions. J. Chem.Eng. Data, 50,1761-1767, 2005; Michael D. Ward, Jeffrey D. Rimer, U.S. Pat. No. 8,450,089; Michael D. Ward, Zina Zhou, U.S. Pat. No. 8,916,609; Hara, et.al U.S. Pat. No. 5,316,767; Longqin Hu, US 2014/0187546.

The present invention is based in part on a surprising finding that compounds, such as cystine, may be incorporated in topical personal care compositions at a skin tolerant pH range, at higher than usual solubility level and as crystals of very small size.

SUMMARY OF THE INVENTION

In one embodiment, the invention includes a process of making a topical personal care composition, the process comprising the steps of:
a. mixing from about 0.5 to about 10% of cystine in basic aqueous solution at pH of from 9 to 14, to obtain an aqueous solution of cystine;
b. mixing the aqueous solution of cystine with a fatty acid—soap lamellar liquid crystal or lamellar gel phase, to obtain the composition comprising cystine in a water phase in solubilized state or in the form of crystals wherein from 90 to 100% of the crystals are in the size from 100 nm to 20 microns
wherein the pH of the composition is in the range of from 3.5 to 8.5.

DETAILED DESCRIPTION OF THE INVENTION

Throughout the specification and claims, the following terms take the meanings explicitly associated herein, unless the context clearly dictates otherwise.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention. In addition, each of the examples given in connection with the various embodiments of the invention which are intended to be illustrative, and not restrictive.

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified. The disclosure of the invention as found herein is to be considered to cover all embodiments as found in the claims as being multiply dependent upon each other irrespective of the fact that claims may be found without multiple dependency or redundancy. In specifying any range of concentration or amount, any particular upper concentration can be associated with any particular lower concentration or amount.

"Comprising" is intended to mean "including" but not necessarily "consisting of" or "composed of." In other words, the listed steps or options need not be exhaustive.

"Skin" is meant to include skin on the face, neck, chest, back, arms (including underarms), hands, legs, buttocks and scalp.

"Leave-on composition" refers to a composition that is applied to the skin and is not intended to be washed or rinsed off for some period of time, specifically hours, as contrasted with skin cleansing or wash-off or rinse-off compositions which are rinsed off or washed off immediately or minutes after the application.

"Non-solid" with respect to the composition means that the composition has a measurable viscosity (measurable for instance with a Brookfield Viscometer DV-I+(20RPM, RV6, 30 Seconds, 20° C.) in the range of from 1 Pas to 500 Pas, preferably from 2 Pas to 100 Pas, more preferably from 3 Pas to 50 Pas.

"Personal care composition" refers to any product applied to a human body for improving appearance, sun protection, cleansing, odor control, moisturization or general aesthetics. Non-limiting examples of personal care compositions include skin lotions, creams, gels, lotions, sticks, shampoos, conditioners, shower gels, toilet bars, antiperspirants, deodorants, shave creams, depilatories, lipsticks, foundations, mascara, sunless tanners and sunscreen lotions.

"Skin cosmetic composition" refers to any product applied to a human body for improving appearance, sun protection, reducing wrinkled appearance or other signs of photoaging, odor control, skin lightening, even skin tone, or general aesthetics. Non-limiting examples of topical cosmetic skin compositions include skin lotions, creams, gels, sticks, antiperspirants, deodorants, lipsticks, foundations, mascara, liquid or gel body washes, soap bars, sunless tanners and sunscreen lotions.

Personal care composition prepared by the present technology is preferably a leave-on non-solid skin cosmetic composition, because such compositions are the most challenging in terms of incorporating cystine due to its low solubility. Increased solubility of cystine in the compositions increases availability of cystine for greater delivery through skin and improved skin feel of the composition (reduces grittiness).

In one embodiment, the compositions of the invention are made by the process according to the invention.

In one embodiment, the process according to the invention includes the steps of:

Step a.: mixing from 0.5 to 10%, or 0.5 to 1.3%, of cystine in basic aqueous solution at pH of from 9 to 14, or 9 to 12, or 9 to 10, to obtain an aqueous solution of cystine. The basic aqueous solution is prepared with a suitable strong base, including but not limited to alkali and alkaline metal hydroxides, monoethanol amine, diethanol amine, triethanol amine, and mixtures thereof. The higher the amount of cystine the higher the pH of the basic solution is required. The solution is prepared at room temperature using a gentle agitation until no visible crystals are seen.

Step b.: mixing the aqueous solution of cystine with fatty acid—soap lamellar liquid crystal or lamellar gel phase, to obtain the composition comprising cystine in a water phase in solubilized state or in the form of crystals wherein from 90 to 100% of the crystals are in the size from 100 nm to 20 microns When cystine is added from a high pH solution to fatty acid-soap lamellar liquid crystal or lamellar gel, this results in limited crystal growth of cystine with average particle size of cystine of less than 20 micrometers. In addition to the small particle size of cystine we have also unexpectedly found that Cystine also remains solubilized to a level from 150 ppm to 1000 ppm when added to and neutralized with fatty acids.

Thus the invention achieves both cystine crystal size less than 20 micrometers to ensure formulation is sensorially pleasing and not gritty while at the same time providing the desired enhanced solubility of cystine from 150 ppm to 1000 ppm. An additional unexpected benefit observed when Cystine is added by the inventive process as compared to when it is added over the side i.e. not by the inventive process is better homogeneity of cystine throughout the formulation. This would ensure better surface coverage of cystine when applied from a product to the skin potentially enhancing its bioavailability and efficacy. Finally having cystine in form of small crystals also enables faster dissolution rate as compared to much larger cystine crystals.

Fatty acid must be neutralized to a level to ensure the formation of a lamellar liquid crystal or lamellar gel phase. Generally speaking the lamellar liquid crystal or lamellar gel phase for fatty acid neutralized system will form at a mole ratio of between 10:1 to 1:10 (Fatty acid:Soap). In one embodiment, the fatty acid to soap mole ratio is between 5:1 to 1:5. Alternatively, the ratio is between 3:1 and 1:3. The amount and temperature at which the lamellar liquid crystal or lamellar gel phase forms is also dependent on fatty acid chain length and type and the amount of water present in the formulation. In the vanishing cream base the lamellar liquid crystal or lamellar gel forms at a temperature of between 50-60° C.

The size of crystals can be estimated by microscopy.

In one embodiment, fatty acids that are employed have a chain length in the range of from C10 to C22. In one embodiment fatty acids have chain length in the range of from C14 to C20, or in the alternative C16 and/or C18. In one embodiment the fatty acid is a mixture of C16 and C18 in a weight ratio of from 2:1 to 1:2.

In one embodiment, the pH of the personal care composition is between 3.5 and 8.5. In some embodiments, the pH of the personal care composition is between pH 3.5 and pH 8. In some embodiments, the pH of the personal care composition is between pH 5 to pH 7.8. In some embodiments, the pH of the personal care composition is between 5 and 7.5.

All additional ingredients as described below can be incorporated into the composition at any point provided they do not completely disrupt the formation of lamellar liquid crystal or lamellar gel phase.

The compositions may include additional oils.

Suitable oils include emollients, fatty acids, fatty alcohols, thickeners and combinations thereof. These may be in the form of silicone oils, natural or synthetic esters, hydrocarbons, alcohols and fatty acids. Amounts of the emollients may range anywhere from 0.1 to 95%, preferably between 1 and 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from $5 \times 10^{-6}$ to $0.1$ m$^2$/s at 25° C. Among the preferred nonvolatile emollients useful in the present compositions are the polydimethyl siloxanes having viscosities from $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the Ester Emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from 0.1 to 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Preferred are emollients that can be used, especially for products intended to be applied to the face, to improve sensory properties and are chosen from the group of polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

The compositions of the present invention preferably include additional ingredients to enhance the ability of cystine to enable intracellular GSH synthesis. In one embodiment, the composition comprises additional amino acids, especially either glycine or glutamate or both. Amino acids included in the inventive composition are present as L stereo isomers, since this is the most abundant and natural isomeric form found in nature. Since the building blocks of naturally-occurring proteins found in human skin, hair and nails are amino acids with the L isomeric form, it is expected that L stereo isomer amino acids contained within personal care products of the present invention can have a greater interaction with these proteins that is intrinsically more biocompatible in nature compared to the D stereo isomeric form. In addition, commercial production and supply of L stereo isomer amino acids is significantly higher compared to the D stereo isomeric form. Finally, L stereo isomer amino acids are also more cost effective to produce, more sustainable, more eco-friendly and available at a lower cost compared to D stereo isomer amino acids.

Any of the amino acids included in the present invention may be in the form of a salt, and the term "cystine," "glutamate source", and "glycine" used in the present specification also encompasses salts. Such salt is not particularly limited as long as it is acceptable for topical application. For example, salts with inorganic acid or organic acid can be mentioned. As the inorganic acid, for example, hydrochloric acid, hydrobromic acid, nitric acid, sulfuric acid, phosphoric acid and the like can be mentioned, and as the organic acid, formic acid, acetic acid, trifluoroacetic acid, propionic acid, lactic acid, tartaric acid, oxalic acid, fumaric acid, maleic acid, citric acid, malonic acid, methanesulfonic acid and the like can be mentioned. As the salt with a base, for example, alkali metal salts such as sodium salt, potassium salt and the like, alkaline earth metal salts such as calcium salt, magnesium salt and the like, and the like can be mentioned.

Glutamate source can be present in the form of its functional equivalents—glutamine, glutamic acid and/or pyroglutamic acid and/or their salts may be employed. Pyroglutamic acid (and/or salts thereof) is preferred since it is more stable than glutamine or glutamic acid. In one embodiment, amino acids in GSH precursor are cystine and pyroglutamic acid (and/or salts thereof). In one embodiment, amino acids in GSH precursor are cystine and pyroglutamic acid and glycine (and/or salts thereof).

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and glycine, at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate, and glycine at pH of 3.5 to 8.5, especially at pH of 5 to 8.

In one embodiment, glutamate source (preferably pyroglutamate) is included in an amount of from 0.01 to 10%, or in the alternative of from to 0.01 to 5%, or from 0.05 to 1%, or in the alternative from 0.05 to 0.5%. In one embodiment, glycine source is included in an amount of from 0.01 to 10%, or in the alternative of from to 0.01 to 5%, or from 0.05 to 1%, or in the alternative from 0.05 to 0.5%.

Thickeners or rheology modifiers can be utilized as part of the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, or from 0.01 to 0.5%.

Humectants of the polyhydric alcohol-type can be included. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from 0.2 to 30%, and preferably from 0.5 to 20%, optimally from 1% to 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra (hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea. Where the term hydroypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from 0.01 to 20%, or from 0.5 to 15%, or from 2 to 10%.

When ammonium salt and substituted urea are used, in a most especially preferred embodiment at least from 0.01 to 25%, or from 0.2 to 20%, or from 1 to 15% humectant, like glycerine, is used. Further moisturizing agents for use herein include petrolatum and/or various aquaporin manipulating actives and/or oat kernel flour.

In some embodiments, the personal care composition, and especially a leave-on skin cosmetic composition of the present invention contains sun-screen. These are typically a combination of organic and inorganic sunscreens. It is particularly important to include both UV-A and UV-B radiation sunscreens.

UV-B sunscreen oil may be selected from the class of cinnamic acid, salicylic acid, diphenyl acrylic acid, or derivatives thereof. The UV-B sunscreen oil may include one or more of octyl salicylate, 3,3,5-trimethylcyclohexyl 2-hydroxybenzoate, ethylhexyl salicylate, 2-ethylhexyl 2-cyano-3,3-diphenyl-2-propenoate, or 2-ethylhexyl-4-methoxycinnamate (also known as octyl methoxycinnamate or "OMC"). Such UV-B sunscreen oils are typically commercially available, such as Octisalate™ (octyl salicylate), Homosalate™ (3,3,5-trimethyleyclohexyl 2-hydroxybenzoate), NeoHeliopan™ (a range of organic UV filters including OMC (Neo Heliopan AV™) and ethylhexyl salicylate (Neo Heliopan OS™)), Octrocryleneu and Milestab 3039™ (2-ethylhexyl-2-cyano-3,3-diphenyl-2-propenoate) or Parsol MCX™ (2-ethylhexyl-4-methoxycinnamate). The amount of UV-B sunscreen oil in the personal care composition may be 0.1 wt % to 20 wt %, or 0.2 wt % to 10 wt %, or 0.5 wt % to 7 wt %, or 2 wt % to 6 wt %.

The personal care composition may further include a UV-B sunscreen that is water-soluble. The water soluble UV-B sunscreen may also include phenylbezimidazole sulfonic acid (also known as ensulizole), 4-aminobenzoic acid (also known as para-aminobenzoic acid or "PABA"), or both.

The personal care composition of any one of the above embodiments may further include 0.1 wt % to 10 wt % of a UV-A sunscreen oil. The UV-A sunscreen oil may include one or more of 4-t-butyl-4'-methoxydibenzoylmethane ("avobenzone"), 2-methyldibenzoylmethane, 4-methyldibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxy-dibenzoylmethane, 2-methyl-5-tert-butyl-4'-methoxy-dibenzoylmethane, 2,4-dimethyl-4'-methoxydibenzoylmethane, 2,6-dimehyl-4-tert-butyl-4'methoxy-dibenzoylmethane, diethylaminohydroxybenzoyl hexyl benzoate, ecamsule, or methyl anthranilate. The amount of UV-A sunscreen oil in the personal care composition may be 0.5 wt % to 7 wt %, or 1 wt % to 5 wt %.

Additional suitable sunscreen oils suitable for use in the personal care composition include those commercially available from BASF corporation: Uvinul T-150 (Ethylhexyl triazone; a UV-B sunscreen oil), Uvinul A Plus (Diethylamino hydroxybenzoyl hexyl benzoate; a UV-A sunscreen oil), Tinosorb S (bis-ethylhexyloxyphenol methoxyphenyl triazine; a UV-A and UV-B sunscreen oil), Tinosorb M(methylene bisbenzotriazolyl tetramethylbutylphenol; a UV-A and UV-B sunscreen oil). Bisdisulizone disodium may also be included in the personal care composition.

A particularly preferred combination of UV-A and UV-B sunscreen oils is avobenzone and 2-ethylhexyl-4-methoxycinnamate.

In some embodiments, the sunscreen is an inorganic sunscreen. Examples of inorganic sunscreens suitable for use in the skin care composition of the present invention include, but are not limited to, microfine titanium dioxide, zinc oxide, polyethylene and various other polymers. By the term "microfine" is meant particles of average size ranging from 10 to 200 nm, alternatively from 20 to 100 nm. Amounts of the sunscreen when present in a skin care formulation according to some embodiments of the present invention may range from 0.1% to 30%, alternatively from 2% to 20%, alternatively from 4% to 10% by weight of the composition.

It has been taught that selenium source, e.g. selenomethionine, is an essential ingredient, along with constituent amino acids of GSH, for enabling GSH intracellular biosynthesis. It has been found as part of the present invention, however, that a selenium source is not necessary, and is indeed superfluous, to achieve intracellular increase in GSH content according to the present invention. Although selenium source may be included, it is preferably avoided in topical skin care compositions of the invention because it is considered a skin sensitizer under some regulatory regimes. Accordingly, the amount of selenium in the present compositions is from 0 to maximum 0.1%, or at most 0.05%, optimally no more than 0.01%.

The inventive composition preferably includes a skin lightening compound, to obtain optimum skin lightening performance at an optimum cost. Illustrative substances are placental extract, lactic acid, resorcinols (4-substituted, 4,5-disubstituted, and 4,6 di-substituted, in particular 4-hexyl, 4-methyl, 4-butyl, 4-isopropyl, phenylethyl resorcinols), arbutin, kojic acid, ferulic acid, nicotinamide and derivatives, hydroquinone, resorcinol derivatives including di-substituted resorcinols and combinations thereof. In one embodiment, such skin lightening compound is a tyrosinase inhibitor, most preferably a compound selected from the group consisting of kojic acid, nicotinamide or derivatives, hydroquinone and other (non-4 substituted resorcinols). Also, dicarboxylic acids represented by the formula HOOC—(CxHy)—COOH where x=4 to 20 and y=6 to 40 such as azelaic acid, sebacic acid, oxalic acid, succinic acid, fumaric acid, octadecenedioic acid (e.g. Arlatone DC) or their salts or a mixture thereof, most preferably fumaric acid or salt thereof, especially di-sodium salt. It has been found that combination with 12HSA with fumaric acid or salts thereof are particularly preferred, especially for skin lightening formulations. Amounts of these agents may range from 0.1 to 10%, preferably from 0.5 to 2% by weight of the composition. It is preferred that the skin lightening coactive according to the invention is nicotinamide, and/or 4-alkyl resorcinol and/or 12-hydroxy stearic acid.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, or from 0.01% to 2%, retinoid. Retinol is preferably used in an amount of 0.01% to 0.15%; retinol esters are preferably used in an amount of from 0.01% to 2% (e.g., 1%); retinoic acids are preferably used in an amount of 0.01% to 0.25%; tocopheryl-retinoate, adapalene, and tazarotene are preferably used in an amount of from 0.01% to 2%.

A variety of herbal extracts may optionally be included in compositions of this invention. Illustrative are pomegranate, white birch (Betula Alba), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1 M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from 0.000001 to 10%, preferably from 0.0001 to 1%.

The personal care composition may further include about 0.1 wt % to about 8 wt % of a film forming polymer. Such film-forming polymers include, but are not limited to, poly-alkyleneoxy terminated polyamides (e.g., INCI name: Polyamide-3, Polyamide-4), polyether polyamides (e.g., INCI name: Polyamide-6), mixed acid terminated polyamides (e.g., INCI name: Polyamide-7), and ester terminated poly (ester-amides) (e.g., INCI name: Polyamide-8). Such film forming polymers may be synthesized or are available commercially, such as under the Sylvaclear™ line of products by Arizona Chemical Company, LLC and the Oleo-Craft™ line of products by Croda International PLC. Film-forming polymers also include, but are not limited to, the INCI named Polyester-5 (e.g., Eastman AQTM 38S Polymer), PPG-17/IPDI/DMPA Copolymer (e.g., Avalure™ UR 450 Polymer), Acrylates Copolymer (e.g., Avalure™ AC 120 Polymer), and polysaccharides such as Xilogel (tamarin gum),lotus bean gums, tara gum, beta glucan, pullulan, carboxymethyl cellulose, hydroxypropyl cellulose, sodium alginate, potato starch, carrageenan. The film forming polymer may include combinations of any two or more of the polymers recited above. The amount of film forming polymer in the personal care composition may be 0.1 wt % to 8 wt. %.

Preservatives can desirably be incorporated into the compositions of this invention to protect against the growth of potentially harmful microorganisms. Suitable traditional preservatives for compositions of this invention are alkyl esters of parahydroxybenzoic-acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, caprylyl glycol, $C_{1-6}$ parabens (especially, methyl paraben and/or propyl paraben), imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2%. An especially preferred combination is octocrylene and caprylyl glycol, since caprylyl glycol has been disclosed to enhance UVA and UVB protection.

Anti-fungal agents suitable for inclusion in personal care compositions are well known to one of skill in the art. Examples include, but are not limited to, climbazole, ketoconazole, fluconazole, clotrimazole, miconazole, econazole, etaconazole, terbinafine, salts of any one or more of these (e.g., hydrochloride salts), zinc pyrithione, selenium disulfide, and combinations of any two or more thereof.

In some embodiments, the personal care compositions of the present invention include vitamins. Illustrative vitamins are Vitamin A (retinol), Vitamin B2, Vitamin B3 (niacinamide), Vitamin B6, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. In some embodiments, the Vitamin B6 derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001% to 10%, alternatively from 0.001% to 10%, alternatively from 0.01% to 10%, alternatively from 0.1% to 10%, alternatively from 1% to 10%, alternatively from 0.01% to 1%, alternatively from 0.1% to 0.5%.

In some embodiments, the personal care compositions of the present invention include an enzyme such as, for example oxidases, proteases, lipases and combinations thereof. In some embodiments, the personal care compositions of the present invention includes superoxide dismutase, commercially available as Biocell SOD from the Brooks Company, USA.

In some embodiments, the personal care compositions of the present invention include desquamation promoters. In some embodiments, the personal care compositions of the present invention include desquamation promoters at a concentration from 0.01% to 15%, alternatively from 0.05% to 15% alternatively from 0.1% to 15%, alternatively from 0.5% to 15%.

Illustrative desquamation promoters include monocarboxylic acids. Monocarboxylic acids may be substituted or unsubstituted with a carbon chain length of up to 16. In some embodiments, the carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids include glycolic, lactic, malic and tartaric acids. In some embodiments, the salt is ammonium lactate. In some embodiments, the beta-hydroxycarboxylic acid is salicylic acid. In some embodiments, the phenolic acids include ferulic acid, salicylic acid, kojic acid and their salts.

In some embodiments, the at least one additional component may be present from 0.000001% to 10%, alternatively from 0.00001% to 10%, alternatively from 0.0001% to 10%, alternatively from 0.001% to 10%, alternatively from 0.01% to 10%, alternatively from 0.1% to 10%, alternatively from 0.0001% to 1% by weight of the composition. Colorants, opacifiers or abrasives may also be included in compositions of the present invention. The colorants, opacifiers or abrasives may be included at a concentration from 0.05% to 5%, alternatively between 0.1% and 3% by weight of the composition.

In some embodiments, the personal care product of the present invention may also include a peptide, such as, for example, the commercially available pentapeptide derivative-Matrixyl™, which is commercially available from Sederma, France. In another example, in some embodiments, the personal care product of the present invention may also include Carnosine.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the topical cosmetic skin careindustry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and nicotinamide, at pH of 3.5 to 8.5.

In one embodiment, the composition of the invention is a leave-on non-solid composition in the form of a personal care topical emulsion, lotion, gel, cream, or vanishing cream comprising glutathione precursor which comprises cystine, glycine, and nicotinamide, at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and nicotinamide at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and one or more of 4-hexylresorcinol, 4-ethylresorcinol, 4-isopropylresorcinol, 4-butylresorcinol, and 4-(1-phenylethyl)resorcinol, at pH of 3.5 to 8.5.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-hexylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-butylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine and 4-(1-phenylethyl)resorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 2-cyclopentyl-5-pentylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 5-pentyl-2-isopropylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine and 5-ethyl-2-cyclopentyl-resorcinol at pH of 3.5 to 8.5, especially at pH of 5 to 8.

Form of the Composition

The compositions of the invention may be used as is. Alternatively, the composition of the present invention may be a component of final product which is water-in-oil or oil-in-water or multiple emulsions. The compositions of the invention are preferably leave-on compositions. The compositions of the present invention are preferably leave-on compositions to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physicochemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it is necessary to minimize the total level of surfactant and the total level of anionic surfactant in leave-on compositions. The total level of surfactant in the inventive compositions is preferably from 1% no more than 15%, more preferably below 10%, most preferably at most 9%, optimally at most 6%.

In some embodiments, anionic surfactants are present in the leave-on skin care composition in an amount of 0.01% to at most 5% by weight of the composition, alternatively from 0.01% to 4% by weight of the composition, alternatively from 0.01% to 3% by weight of the composition, alternatively from 0.01% to 2% by weight of the composition, alternatively substantially absent (less than 1%, or less than 0.1%, or less than 0.01%). In some embodiments, the total level of surfactant in the skin care compositions is no more than 15%, alternatively below 10%, alternatively at most 9%.

In some embodiments, the surfactant is selected from the group consisting of anionic, nonionic, cationic and amphoteric actives.

In some embodiments, nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. In some embodiments, the non-ionic surfactant is selected from the group consisting of alkyl polyglycosides, saccharide fatty amides (e.g. methyl gluconamides) and trialkylamine oxides.

Amphoteric surfactants suitable in skin care compositions according to some embodiments of the present invention include cocoamidopropyl betaine, $C_{12}$-$C_{20}$ trialkyl betaines, cocoamidopropyl hydroxysultaine, sodium lauroamphoacetate, and sodium laurodiamphoacetate.

Anionic surfactants suitable in skin care compositions according to some embodiments of the present invention include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

The most preferred format are vanishing cream base and creams or lotions based on oil-in-water emulsions. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hystric acid which is substantially (generally about 90 to 95%) a mixture of stearic acid and palmitic acid. A typical hystric acid comprises about 52-55% palmitic acid and 45-48% stearic acid of the total palmitic-stearic mixture. Thus, inclusion of hystric acid and its soap to prepare the vanishing cream base is within the scope of the present invention. It is particularly preferred that the composition comprises higher than 7%, preferably higher than 10%, more preferably higher than 12% fatty acid. A typical vanishing cream base is structured by a crystalline network and is sensitive to the addition of various ingredients.

In some embodiments the personal care composition is formulated as a shampoo. In some embodiments, the personal care compositions of the present invention are formulated as a deodorant. In some embodiments, the personal care compositions of the present invention are formulated as an antiperspirant, e.g. according to the formulations described in U.S. Pat. No. 7,282,471.

In some embodiments, the personal care compositions of the present invention are formulated as a single use personal care towelette product as a single use personal care towelette product according to the formulations described in U.S. Pat. No. 7,282,471.

Method of Using the Skin Care Compositions

In some embodiments, the skin care composition is topically applied to human skin. In some embodiments, the skin care composition provides at least one benefit, selected from the group consisting of: skin conditioning, skin smoothening, reduction of wrinkled or aged skin, reduction of inflammation of the skin, reduction of dryness, reduction of age spots, an reduction of sun burn, and lightening of the skin.

In some embodiments, a small quantity of the skin care composition, for example from 1 to 5 ml, is applied to exposed area of the skin, from a suitable container or applicator and, if necessary, it is then spread over and/or rubbed into the skin using the hand or fingers or a suitable device. Alternatively, a small quantity of the skin care composition, for example from 1 to 5 ml, is applied to exposed area of the skin, from a suitable container or applicator and then covered by mask, non-woven, or film-former.

Reference is now made to the following examples, which together with the above descriptions illustrate some embodiments of the invention in non-limiting examples.

EXAMPLE 1

Example 1 investigated cystine recrystallization from high pH solution.

The soap/acid emulsions were prepared using hystric acid (55% palmitic acid/45% stearic acid) by melting the hystric acid at 75° C. and adding this melted acid to aqueous phase consisting of KOH. This resulted in formation of the acid/soap mixture which has the paste like consistency. Solubilized cystine in high pH solution was then added to the acid/soap mixture as high pH solution. Depending on the procedure of addition, differences in final formulations have been achieved.

TABLE 1

The acid soap mixtures were prepared according to following batch sheet:

| Sample | A | B | C |
|---|---|---|---|
| Aqueous phase 1 (heated to 75° C.) | | | |
| Water | 79.7 | 77.72 | 77.72 |
| KOH (45%) | 1.2 | 1.17 | 1.17 |
| Cystine | 0.22 | — | — |
| Oil phase (heated to 75° C.) | | | |
| | % weight | % weight | % weight |
| Hystric acid | 18.87 | 18.4 | 18.4 |
| Aqueous phase 2 | | | |
| Cystine solution (8% in 3% NaOH) added at 75° C. | | 2.71 | |
| Cystine solution (8% in 3% NaOH) added at 55° C. | | | 2.71 |
| Cystine crystal size (in microns) | 20-50 | 20-50 | 1-2 |

Formula A was prepared by dissolving the cystine in hot KOH solution. Melted hystric acid was then added to this hot (75° C.) aqueous solution of cystine, mixed and let cool down to room temperature while mixing.

Formula B was prepared by adding the melted hystric acid to hot KOH solution, and adding the high pH solution of cystine while mixing all ingredients at 75° C.

Formula C was prepared by adding the melted hystric acid to hot KOH solution, creating thus soap, cooling the soap to 50° C. and then adding the high pH solution of cystine The resulting acid soap mixtures were observed under microscope for the formation of cystine crystals.

Formula A—at 10× magnification at room temperature showed the formation of cystine crystals of 20-50 microns.

Formula B—at 25× magnification at 80C showed the formation of cystine crystals of 20-50 microns.

Formula C—at 25× magnification at 80C—showed the formation of only very small particles in the range 1-2 microns.

Addition of cystine solution to acid soap mixture at 50-60° C. is preferred as only small particles are formed. At this temperature the majority of acid soap exists in lamellar liquid crystal or lamellar gel with vary narrow aqueous layer creating a restrictive environment for cystine crystal growth. When cystine was added from a high pH solution to fatty acid-soap at a point after which one of the phases that forms is a lamellar liquid crystal or lamellar gel phase, results in limited crystal growth of cystine with average particle size of cystine of less than 20 micrometers. When the same experiment was performed adding cystine at a temperature of 75C-80° C. when it is in the form of oil-in-water emulsion the cystine crystals were much larger with size greater than 20 micrometers (see table 1 and FIGS. 1, 2, 3).

EXAMPLE 2

Additional samples with decreasing concentration of cystine were prepared to find the solubility limit for cystine in acid soap mixture. Samples in table 2 were prepared by Process A in table 1.

TABLE 2

| Sample | D | E | F |
|---|---|---|---|
| Water phase | | | |
| KOH (45%) | 1.2 | 1.2 | 1.2 |
| Cystine | 0.26 | 0.11 | 0.07 |
| Water | QS | QS | QS |
| Oil phase | | | |
| | % w | % w | % w |
| Hystric acid | 18.9 | 18.9 | 18.9 |
| Crystals presence | yes | yes | No |

The samples were evaluated under microscope on the hot plate at 80° C. Samples D and E showed the presence of the cystine crystals, sample F did not contain any crystals, even after 7 days of storage. That corresponds to solubility of cystine of greater than 700 ppm in the hystric acid acid/soap media.

EXAMPLE 3

Example 3 investigated a modified system that included Brij 35 surfactant. The compositional examples are in the table 3 below. The samples in table 3 were prepared by process C in table 1.

TABLE 3

| Sample | G | H | I |
|---|---|---|---|
| Water phase | | | |
| KOH (45%) | 1.2 | 1.2 | 1.2 |
| Cystine | 0.23 | 0.13 | 0.06 |
| Water | QS | QS | QS |
| Oil phase | | | |
| | % w | % w | % w |
| Hystric acid | 19.1 | 19.1 | 19.1 |
| Brij 35 | 2.2 | 2.2 | 2.2 |
| Crystals Presence | yes | yes | no |
| Size (microns) | 1-2 | 1-2 | — |

The results in Table 3 illustrate that other ingredients can be added to the inventive compositions, as long as lamellar bilayer liquid crystal or liquid gel structure remains intact. Similar results were obtained, where solubility was determined at minimal concentration of greater than 600 ppm.

EXAMPLE 4

Additional samples of lamellar liquid crystal or lamellar gel or lamellar gel phase using the nonionic surfactant, instead of fatty acid-soap, were prepared to investigate whether increased solubility due to only lamellar liquid crystal or lamellar gel or lamellar gel phase or also the presence of fatty acids. Additional system was investigated utilizing non-ionic tetraethylene glycol monododecyl ether C12EO4 surfactant. Concentration of this surfactant was selected to form lamellar liquid crystal or lamellar gel or lamellar gel phase in water solution. Cystine was added as high pH solution to lamellar liquid crystal or lamellar gel phase and subsequently was neutralized with citric acid solution. Small crystals were observed at all four prepared concentrations. In this case solubility experiments indicated that the solubility of cystine is below 200 ppm.

TABLE 4

| | no fatty acid | | | |
|---|---|---|---|---|
| Sample | J | K | L | M |
| C12EO4 | 59.3 | 62.5 | 62.1 | 61.5 |
| KOH (45%) | 0.1 | 0.05 | 0.033 | 0.01 |
| cystine | 0.2 | 0.1 | 0.07 | 0.02 |
| citric acid solution, 4% | 2.5 | 1.2 | 0.9 | 0.3 |
| water | QS | QS | QS | QS |
| Crystals present | yes | yes | yes | yes |
| Size of crystals (microns) | 1-2 | 1-2 | 1-2 | 1-2 |

Non-ionic surfactants do not neutralize the high pH solutions of the cystine when mixed, and addition of extra low pH aqueous phase for neutralization was necessary. It can be seen from the results in the above table that the cystine crystals formed were small indicating that the presence of lamellar liquid crystal or lamellar gel phase was limiting the crystal growth. A lamellar liquid crystal or lamellar gel using only an ethoxylated surfactant C12EO4 with citric acid added as acidic solution and to which cystine dissolved in high pH was added. Our results illustrate that although the small crystal size is preserved in this latter case we do not however achieve any enhancement in cystine solubility above its natural solubility of 100 ppm as there is no fatty acid present.

EXAMPLE 5

Solubility of cystine was determined in the presence of alternative fatty acids. The solubility of L cystine in the presence of fatty acids was determined by solubilizing the excess of L-cystine at high pH (in 0.05-0.1% (w) NaOH) and neutralizing the solution with the selected fatty acid or fatty acid mixture to neutral pH in the range of 5-7. The precipitate upon neutralization was equilibrated with saturated solution for at least 72 hours. The solutions were then filtered through 0.45 micrometer PTFE or nylon (for C12) syringe filter and analysed on HPLC for cystine concentration. (Phenomenex Synergi Hydro RP 4 um column, 250× 4.6 mm, Mobile phase −0.2% formic acid in water, isocratic mode, flow rate 1 mL/min, column temperature 30C, UV detector at 250 nm). The results obtained are summarized in the Table 5.

TABLE 5

| Acid | pH | Solubility ppm cystine | % RSD* |
|---|---|---|---|
| Octanoic (C8) | 5.3 | 188.1 | 6.1 |
| Decanoic (C10) | 6.8 | 262.3 | 11.8 |
| Dodecanoic (C12) with NaOH | 7.6 | 575 | 13.4 |
| Dodecanoic (C12) with KOH | 7.6 | 490.6 | 9.5 |
| Oleic acid (C18:1) | 7.3 | 246.8 | 6.6 |
| **C12/Oleic mixture (0.25 molar ratio) | 7.3 | 253 | 2.7 |

TABLE 5-continued

| Acid | pH | Solubility ppm cystine | % RSD* |
|---|---|---|---|
| Malonic | 6.3 | 162.4 | 2.3 |
| Succinic | 6.3 | 150.4 | 7 |
| Adipic | 7 | 171.1 | 7.4 |
| Maleic | 6.6 | 181.6 | 1.5 |

*% RSD specifies the % of relative standard deviation for 3 replicas (% RSD = Standard dev./mean × 100%)
**eutectic mixture of C12/oleic acid Cystine remained solubilized to a level from 150 ppm to 600 ppm when added to and neutralized with fatty acids. The amount solubilized depended on fatty acid type and chain length as highlighted in Table 5.

EXAMPLE 3

Personal care formulations according to the present invention are illustrated in the Tables below. All numbers in the Tables represent weight % in the composition.

TABLE I

| Oil-in-water formulations, lotions, and creams | | | | | |
|---|---|---|---|---|---|
| | OW-1 | OW-2 | OW-3 | OW-4 | OW-5 |
| Water | To 100 | To 100 | To 100 | To 100 | To 100 |
| Glycerine | 0-40 | 1-40 | 1-5 | 1-10 | 1-40 |
| Propylene glycol | 0-5 | | 0-5 | | |
| Butylene glycol | 0-5 | | 0-5 | 0-5 | |
| Carbomer | 0-2 | 0.03-1 | | | |
| Ammonium Acryloyl dimethyl taurate/VP copolymer | 0-1 | | 0.03-1 | | 0.01-1 |
| Styrene/Acrylates copolymer | 0-1 | | 0.01-1 | | |
| Xanthan Gum | 0-1 | | | | 0.01-1 |
| EDTA | 0.01-0.01 | 0.01-0.01 | 0.01-1 | 0.01-1 | 0.01-1 |
| Preservative | 0.02-2 | 0.02-2 | 0.02-2 | 0.02-2 | 0.02-2 |
| Titanium oxide | 0-10 | 0.01-10 | 0.01-10 | 0.01-10 | 0.01-10 |
| Colorant/Pigment | 0-5 | 0-5 | 0-5 | 0-5 | 0-5 |
| Triethanol amine/Sodium Hydroxide/potassium Hydroxide | 0-3 | 0.01-3 | 0.01-3 | 0.01-3 | 0.01-3 |
| Stearic acid | 0-5 | 0.01-5 | 0.01-5 | 0.01-5 | 0.01-5 |
| Isopropyl Myristate | 0-10 | 0.01-10 | | | |
| Capric/Caprylic Triglyceride | 0-10 | 0.01-10 | | | |
| C12-C15 alkyl benzoate | 0-10 | | | | 0.01-10 |
| Mineral oil | 0-10 | | | 0.01-10 | |
| Glyceryl stearate | 0-5 | 0.01-5 | | | |
| Steareth-2 | 0-5 | | 0.01-5 | | 0.01-5 |
| Steareth-21 | 0-5 | | 0.01-5 | | |
| Peg100 Stearate | 0-5 | | | 0.01-2 | 0.01-5 |
| Potassium Cetyl Phosphate | 0-5 | | | 0.01-2 | |
| Tween20 | 0-5 | | | | 0.01-5 |
| Cetyl alcohol | 0-4 | 0.01-4 | | 0.01-4 | |
| Dicaprylyl carbonate | 0-5 | | 0.01-5 | | |
| Ethyl hexyl methoxycinnamate | 0-6 | 0.01-6 | | | |
| Butyl Methoxy-dibenzoylmethane | 0-3 | 0.01-3 | | 0.01-3 | 0.01-3 |
| Ensulizole | 0-4 | | | | 0.01-4 |
| Octinoxate | 0-7.5 | | | | |
| Octisalate | 0-5 | | | 0.01-5 | 0.01-5 |
| Octocrylene | 0-10 | | | 0.01-10 | 0.01-10 |
| Homosalate | 0-10 | | | 0.01-10 | |
| Dimethicone | 0-10 | 0.01-10 | 0.01-10 | | |
| Cyclomethicone | 0-15 | | 0.01-15 | | |
| Niacinamide | 0-5 | 0-5 | 0-5 | 0-5 | 0-5 |
| Fragrance | 0-2 | 0-2 | 0-2 | 0-2 | 0-2 |
| Glutamine/Sodium PCA | 0.01-10 | 0.01-10 | 0.01-10 | 0.01-10 | 0.01-10 |
| Glycine | 0.01-10 | 0.01-10 | 0.01-10 | 0.01-10 | 0.01-10 |
| Cystine | 0.001-2 | 0.001-2 | 0.001-2 | 0.001-2 | 0.001-2 |
| 2-Cyclopentyl-5-pentylresorcinol | 0.001-3 | | | | 0.001-3 |
| 5-pentyl-2-isopropylresorcinol | | 0.001-3 | | | |
| 5-pentyl-2-cyclopentylresorcinol | | | | 0.001-3 | 0.001-3 |

TABLE II

Water-in-oil topical lotions or creams

| | WO-1 | WO-2 | WO-3 | WO-4 |
|---|---|---|---|---|
| Water | To 100 | To 100 | To 100 | To 100 |
| Glycerine | 0-70 | 1-70 | 1-70 | |
| Propylene glycol | 0-5 | | | 0.01-5 |
| Butylene glycol | 0-5 | | 0.01-5 | 0.01-5 |
| Disteardimonium Hectorite | 0.01-1 | 0.01-1 | | |
| EDTA | 0.01-.01 | 0.01-1 | 0.01-1 | 0.01-1 |
| Preservative | 0.02-2 | 0.02-2 | 0.02-2 | 0.02-2 |
| TiO2 | 0-10 | 0.01-10 | 0.01-10 | 0.01-10 |
| Colorant/pigment | 0-5 | 0-5 | 0-5 | 0-5 |
| TEA/Sodium Hydroxide/ potassium Hydroxide | 0-3 | 0.01-3 | 0.01-3 | 0.01-3 |
| Stearic acid | 0-5 | 0.01-5 | | |
| Isopropyl Myristate | 0-10 | | | |
| Capric/Caprylic Triglyceride | 0-10 | | 0.01-10 | |
| C12-C15 alkyl benzoate | 0-10 | | | 0.01-10 |
| Mineral oil | 0-10 | | | |
| Glyceryl stearate | 0-5 | | | |
| Dimethicone copolyol | 0-5 | 0.01-5 | 0.01-5 | |
| Cetyl PEG/PPG-10/1 Dimethicone | 0-5 | | | 0.01-5 |
| Steareth-2 | 0-2 | | | |
| Sucrose Distearate | 0-2 | 0.01-2 | | |
| Cetyl alcohol | 0-2 | 0.01-2 | 0.01-2 | |
| Ethyl hexyl methoxycinnamate | 0-6 | 0.01-6 | | |
| Butyl Methoxy-dibenzoylmethane | 0-3 | 0.01-3 | 0.01-3 | 0.01-3 |
| Ensulizole | 0-4 | | 0.01-4 | |
| Octinoxate | 0-7.5 | | | |
| Octisalate | 0-5 | | 0.01-5 | 0.01-5 |
| Octocrylene | 0-10 | | 0.01-10 | 0.01-10 |
| Homosalate | 0-10 | | | 0.01-10 |
| Dimethicone | 0-10 | | 0.01-10 | 0.01-10 |
| Cyclomethicone | 0-40 | 0.01-40 | | 0.01-40 |
| Caprylyl methicone | 0-10 | 0.01-10 | | 0.01-10 |
| Dimethicone crosspolymer | 0-90 | 0.01-90 | 0.01-90 | |
| C30-C45 alkyl cetearyl dimethicone crosspolymer | | | | 0.01-90 |
| Glycolic acid | 0-10 | 0.01-10 | | |
| KCl | 0-5 | 0.01-5 | 0.01-5 | 0.01-5 |
| Niacinamide | 0-5 | 0.01-5 | 0.01-5 | 0.01-5 |
| Fragrance | 0-2 | 0-2 | 0-2 | 0-2 |
| Glutamine/Sodium PCA | 0.01-10 | 0.01-10 | 0.01-10 | 0.01-10 |
| Glycine | 0.01-10 | 0.01-10 | 0.01-10 | 0.01-10 |
| Cystine | 0.001-2 | 0.001-2 | 0.001-2 | 0.001-2 |
| 4-hexylresorcinol | 0.001-3 | | | |
| 4-ethylresorcinol | | 0.001-3 | | |
| 4-butylresorcinol | | | 0.001-3 | |
| 4-(1-phenyl-ethyl)resorcinol | | | | 0.001-3 |

TABLE III

Vanishing Creams

| | VC-1 | VC-2 | VC-3 | VC-4 |
|---|---|---|---|---|
| Water | To 100 | To 100 | To 100 | To 100 |
| Glycerine | 0-5 | 0.01-5 | 0.01-5 | |
| EDTA | 0.01-.01 | 0.01-.01 | 0.01-.01 | 0.01-.01 |
| Preservative | 0.02-2 | 0.02-2 | 0.02-2 | 0.02-2 |
| TiO2 | 0.01-10 | 0.01-10 | 0.01-10 | 0.01-10 |
| Colorant/pigment | 0-5 | 0.01-5 | 0.01-5 | |
| TEA/Sodium Hydroxide/potassium Hydroxide | 0-3 | 0.01-3 | 0.01-3 | 0.01-3 |
| Stearic acid | 0-30 | 0.01-30 | 0.01-30 | 0.01-30 |
| Isopropyl Myristate | 0-5 | 0.01-10 | 0.01-10 | |
| C12-C15 alkyl benzoate | 0-5 | | | 0.01-10 |
| Brij 35 | 0-5 | 0.01-5 | | |
| Tween40 | 0-5 | | | 0.01-5 |
| Cetyl alcohol | 0-2 | 0.01-2 | 0.01-2 | |
| Ethyl hexyl methoxycinnamate | 0-6 | 0.01-6 | 0.01-6 | |
| Butyl Methoxy-dibenzoylmethane | 0-3 | 0.01-3 | 0.01-3 | 0.01-3 |
| Ensulizole | 0-4 | | | 0.01-4 |
| Octisalate | 0-5 | | | 0.01-5 |
| Octocrylene | 0-10 | | 0.01-10 | 0.01-10 |
| Dimethicone | 0-5 | 0.01-5 | | |
| Cyclomethicone | 0-5 | | | 0.01-5 |
| Dimethicone crosspolymer | 0-4 | | | 0.01-4 |
| Hydroxystearic acid | 0-5 | 0.01-5 | 0.01-5 | 0.01-5 |
| Fragrance | 0-2 | 0-2 | 0-2 | 0-2 |
| Glutamine/Sodium PCA | 0.01-10 | 0.01-10 | 0.01-10 | 0.01-10 |
| Glycine | 0.01-10 | 0.01-10 | 0.01-10 | 0.01-10 |
| Cystine | 0.001-2 | 0.001-2 | 0.001-2 | 0.001-2 |
| Nicotinamide | 0.01-5 | 0.01-5 | 0.01-5 | 0.01-5 |

The invention claimed is:

1. A process of making a topical personal care composition, the process comprising
   a. mixing from about 0.5 to about 10 wt. % of cystine in basic aqueous solution at pH of from about 9 to about 14, to obtain an aqueous solution of cystine;
   b. mixing the aqueous solution of cystine with a fatty acid-soap lamellar liquid crystal or lamellar gel phase at about 50 to about 60 degrees Celsius, to obtain the composition comprising cystine in a water phase in solubilized state or in the form of crystals wherein from about 90 to about 100% of the crystals are in the size from about 100 nm to about 20 microns;
   wherein the pH of the composition is in the range of from about 3.5 to about 8.5;
   wherein the molar ratio of said fatty acid to said soap is from about 10:1 to about 1:10.

2. The process of claim 1 wherein more than 30 wt. % of the topical personal care composition is in form of said lamellar liquid crystal or lamellar gel phase.

3. The process of claim 1 wherein the fatty acid is a $C_{10}$ to $C_{22}$ saturated fatty acid.

4. The process of claim 1 wherein said cystine is solubilized in an amount of from about 150 ppm to 1000 ppm.

5. A topical personal care composition comprising:
   a. at least about 50 wt. % of the topical personal care composition in form of a lamellar liquid crystal or lamellar gel fatty acid-soap phase, wherein the fatty acid is a $C_{10}$ to $C_{22}$ saturated acid; and
   b. an aqueous phase comprising from about 0.001 to about 2 wt. % of cystine wherein said cystine is solubilized or present as crystals in the size range of from about 100 nm to about 20 microns;

wherein the pH of the topical personal care composition is in the range of from about 3.5 to about 8.5;

further wherein the molar ratio of said fatty acid to said soap is from about 10:1 to about 1:10.

6. The composition according to claim 5 wherein the fatty acid is hystric acid.

7. The composition of claim 5 wherein the composition is a leave-on non-solid skin cosmetic composition.

8. The composition of claim 5 wherein the composition is a vanishing cream comprising about 5 to about 40 wt. % said fatty acid and about 0.1 to about 20 wt. % said soap.

9. The composition of claim 5 wherein the composition further comprises an amino acid selected from the group consisting of glutamine, glycine, and mixtures thereof.

\* \* \* \* \*